(12) United States Patent
Karig et al.

(10) Patent No.: US 9,522,904 B2
(45) Date of Patent: *Dec. 20, 2016

(54) METHOD FOR PRODUCING TRIAZINYL-SUBSTITUTED OXINDOLES

(71) Applicant: BAYER INTELLECTUAL PROPERTY GMBH, Monheim (DE)

(72) Inventors: Gunter Karig, Hofheim am Taunus (DE); Mark James Ford, Schmitten (DE); Konrad Siegel, Duesseldorf (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/596,425

(22) Filed: Jan. 14, 2015

(65) Prior Publication Data

US 2015/0126737 A1    May 7, 2015

Related U.S. Application Data

(63) Continuation of application No. 13/995,891, filed as application No. PCT/EP2011/073283 on Dec. 19, 2011, now Pat. No. 8,962,828.

(60) Provisional application No. 61/425,349, filed on Dec. 21, 2010.

(30) Foreign Application Priority Data

Dec. 21, 2010   (EP) .................................... 10196205

(51) Int. Cl.
| | | |
|---|---|---|
| C07D 403/04 | (2006.01) |
| A01N 43/66 | (2006.01) |
| C07D 405/04 | (2006.01) |
| C07D 403/12 | (2006.01) |

(52) U.S. Cl.
CPC ............. *C07D 403/04* (2013.01); *A01N 43/66* (2013.01); *C07D 403/12* (2013.01); *C07D 405/04* (2013.01)

(58) Field of Classification Search
CPC ... C07D 403/04; C07D 251/12; C07D 251/36; A01N 43/66
USPC .................. 544/180, 219, 218, 217; 504/230
See application file for complete search history.

(56) References Cited

U.S. PATENT DOCUMENTS

| | | | |
|---|---|---|---|
| 6,265,411 B1 | 7/2001 | Thomas et al. | |
| 8,962,828 B2 * | 2/2015 | Karig et al. .................. | 544/180 |
| 8,969,553 B2 * | 3/2015 | Karig et al. .................. | 544/180 |
| 2004/0116388 A1 | 6/2004 | Armistead et al. | |
| 2007/0281949 A1 | 12/2007 | Bacon et al. | |
| 2009/0291982 A1 | 11/2009 | Claesson et al. | |

FOREIGN PATENT DOCUMENTS

| | | |
|---|---|---|
| JP | 2000044546 A | 2/2000 |
| WO | 0125220 A1 | 4/2001 |
| WO | 02083654 A1 | 10/2002 |
| WO | 03082853 A1 | 10/2003 |
| WO | 2005027823 A2 | 3/2005 |
| WO | 2005061519 A1 | 7/2005 |
| WO | WO 2006008159 A1 * | 1/2006 |
| WO | 2006136606 A2 | 12/2006 |
| WO | 2007089193 A1 | 8/2007 |

OTHER PUBLICATIONS

Kang et al., "a-Arylation of 3-ARyloxindoles", Organic Letters (2010) vol. 12, No. 10, pp. 2306-2309.
Science of Synthesis (2000) vol. 10, pp. 600-619.
Laurent F. Hennequin et al. "Novel Synthesis of Oxindole Quinazolines Using Solid Phase Multiparallel Chemistry", Etrahedron Letiers, vol. 40 (1999) pp. 3881-3884.
Altman et al."Orthogonal Pd- and Cu-Based Catalyst System for C- and N-Arylation of Oxindoles", J. Am Chem. Soc., vol. 130, (2008) pp. 9613-9620.
Taylor "Palladium-Catalyzed Enantioselective A-Arylation and A-Vinylation of Oxindoles Faciliated by an Axially Chiral P-Stereogenic Ligand", J. Am Chem. Soc., vol. 131, (2009) pp. 9900-9901.
Ding et al. "Structure-Based Design of Spiro-Oxindoles as Potent, Specific Small-Molecule Inhibitors of the MDM2-P53 Interaction", J. Med Chem., (2006) vol. 49, pp. 3432-3435.
Shen et al. "A-Heteroaylation of Esters, Lactones, Amides, and Lactams by Nucleophilic Aromatic Substitution", Orgainc Letiers, vol. 8, No. 7 (2006), pp. 1447-1450.
Durbin et al. "Palladium-Catalyzed A-Arylation of Oxindoles", Organic Letiers, vol. 10, No. 7 (2008), pp. 1413-1415.
Volk "Raney Nickel-Induced 3-Alkylation of Oxindole With Alcohols and Diols", Synthesis, No. 5 (2002), pp. 595-597.
Mai et al. "A-Arylation of 3-Arylation of 3-Aryloxindoles", Organic Letiers, vol. 12, No. 10 (2010), pp. 2306-2309.
International Search Report for PCT/EP2011/073283 Mailed Jun. 6, 2012.

* cited by examiner

*Primary Examiner* — Venkataraman Balasubramanian
(74) *Attorney, Agent, or Firm* — McBee Moore Woodward Vanik IP LLC

(57) ABSTRACT

Process for the preparation of triazinyl-substituted oxindoles of formula (3)

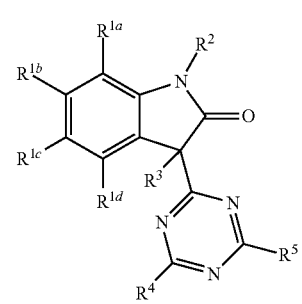

(3)

and salts thereof by reacting an oxindole (1) with a triazine (2) in the presence of a carbonate, a hydroxide, a phosphate or a mixture of two or more of the aforementioned compounds, and also the compounds of formula (3) and salts thereof (3") and the use of both for producing crop protection agents.

1 Claim, No Drawings

METHOD FOR PRODUCING TRIAZINYL-SUBSTITUTED OXINDOLES

This application is a continuation application of application Ser. No. 13/995,891, filed Sep. 16, 2013, which is a 371 of PCT/EP2011/73283, filed Dec. 19, 2011, which claims priority to EP 10196205.8, filed Dec. 21, 2010, which claims the benefit of 61/425,349, filed Dec. 21, 2010), the contents of which are incorporated herein by reference in their entireties.

BACKGROUND OF THE INVENTION

Field of the Invention

The present application relates to improved processes for the preparation of triazinyl-substituted oxindoles and their use as intermediates for the synthesis of fine chemicals and of active ingredients in the field of agriculture.

Description of Related Art

Oxindoles substituted in the 3 position are an important structural motif among a series of natural substances and pharmaceutically effective substances. Some of these compounds exhibit biological activity against various pathogens and have e.g. antitumor or anti-HIV properties (Ding et al., *J. Med. Chem.* 2006, 49, 3432; Jiang et al., *Bioorg. Med. Chem. Lett.* 2006, 16, 2105).

A further subgroup of the oxindoles substituted heteroaromatically in the 3 position are the 3-triazinyloxindoles (3-(1,3,5-triazin-2-yl)-1,3-dihydro-2H-indol-2-one. The preparation of these compounds, referred to by the trivial name of "3-triazinyloxindoles", is the subject of the present invention.

It is known that a hydrogen bonded to an aromatic, heteroaromatic or to an aliphatic carbon backbone can be exchanged for functional substituents which may likewise be aromatic, heteroaromatic or aliphatic.

In this connection, it is interesting that the reaction conditions for the substitution of the hydrogen in the 3 position of oxindoles are different depending on the nature of the substituents. Accordingly, the reaction conditions for the exchange for aliphatic, aromatic and heteroaromatic radicals have been researched and developed independently of one another.

Standard reactions of the substitution of oxindoles in the 3 position include the exchange of hydrogen for aliphatic substituents (*Science of Synthesis*, 10 (2000), p. 600).

The exchange for aromatic substituents in the presence of palladium was described by Taylor et al. (*J. Am. Chem. Soc.*, 2009, 131, 9900-9901), and also by Altman et al. (*J. Am. Chem. Soc.* 2008, 130 (29), 9613-9620), and also by Durbin et al. (*Org. Lett.*, 2008, 10 (7), 1413-1415).

The synthesis of substituted oxindoles in which the hydrogen have been exchanged for heteroaromatic 6-ring substituents has likewise been described. By way of example, mention is made here of the substitution in the 3 position of N-methyl-oxindole with a substituted pyridazine (Shen et al., *Org. Lett.*, 2006, 8, 1447-1450), the preparation of substituted 3-(quinazolin-4-yl)oxindoles (U.S. Pat. No. 6,265,411), the substitution in the 3 position of oxindole with substituted quinazolines over a solid phase (Hennequin et al., *Tetrahedron Lett.*, 1999, 40, 3881-3884), the substitution with substituted pyridines or pyridine N-oxides (e.g. US 2009/291982, WO 2007/89193, WO 2005/27823, WO 2003/82853), the preparation of substituted 3-(pyrimidin-4-yl)oxindoles (WO 2006/136606, WO 2003/82853, US 2007/281949) or the preparation of substituted 3-(2H-pyrazolo[3,4-d]pyrimidin-4-yl)oxindoles (US 2007/281949).

According to Scheme 1, 3-triazinyloxindoles can be obtained by exchanging a hydrogen atom in the 3 position of an optionally substituted oxindole (1) for an optionally substituted triazine (2) which carries a suitable leaving group X, in the presence of a "suitable" base.

Scheme 1 - Synthesis of 3-triazinyloxindoles:

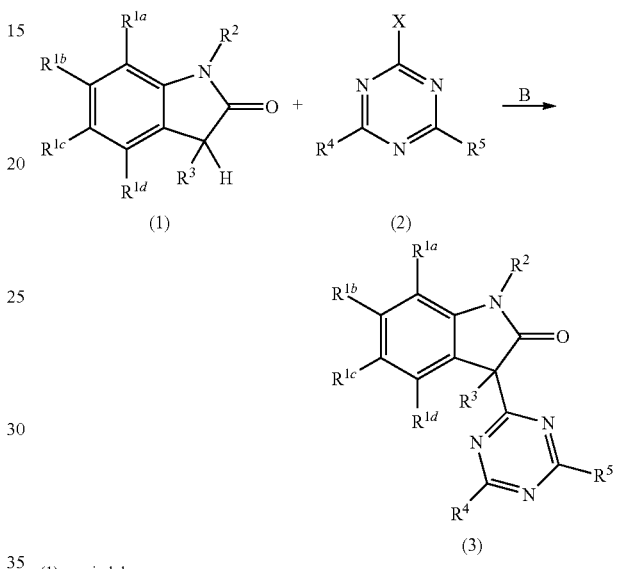

(1) = oxindole
(2) = triazine with X as leaving group
B = base

In this connection, it is known that the step of deprotonation of the oxindole that is important for the exchange of the hydrogen can be influenced in a targeted manner through the choice of substituent $R^3$.

A common feature of the reactions disclosed in the aforementioned prior art is that the oxindole used is firstly deprotonated with a strong base and then the heterocyclic component, typically as chlorine compound, is added.

For the purposes of the deprotonation, in the prior art, strong, water-sensitive bases, such as sodium hexamethyldisilazane or lithium diisopropylamide (LDA), sodium hydride or lithium hydride, are used.

Disadvantageously, the use of the bases sodium hydride and lithium hydride leads to the formation of equimolar amounts of elemental hydrogen. Moreover, the solvents used in connection with these bases have to be laboriously dried prior to being used.

An analogous coupling—analogous to the coupling of oxindoles with quinolines described in WO 2005/061519, in which quinoline N-oxides are used in the presence of acidic anhydride—with triazines of formula (2) is not known.

Scheme 2 summarizes a known process for the preparation of substituted 3-triazinyloxindoles. These are characterized in that they carry nitrogen substituent on the triazine ring. The synthesis is disclosed in US 2004/116388, WO 2002/083654 and WO 2001/025220.

Scheme 2 - Synthesis of N-substituted 3-triazinyloxindoles:

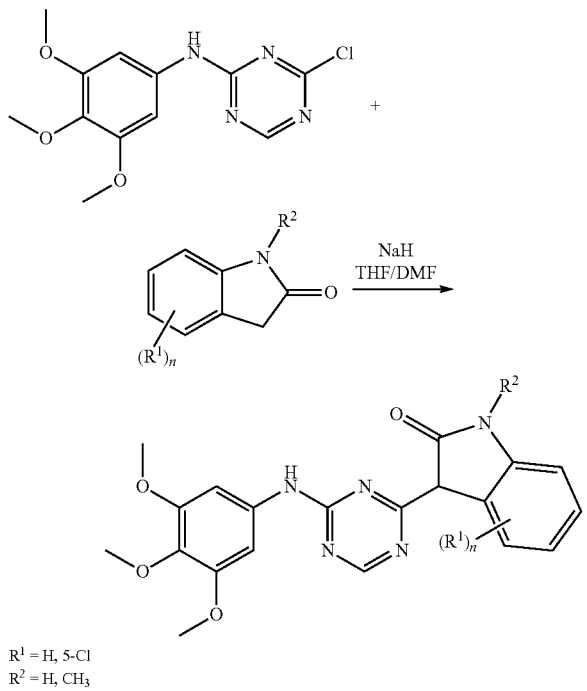

R¹ = H, 5-Cl
R² = H, CH₃

In the reaction according to Scheme 2, a substituted 4-chloro-N-phenyl-1,3,5-triazine-2-amine was used as triazine-containing component. The reaction was carried out by deprotonation of the oxindole used in DMF/THF with sodium hydride, followed by the addition of the triazine component and subsequent stirring of the reaction mixture at 80° C.

Disadvantageously, the achieved yields for this known synthesis are only 2.5%, or 7% for the oxindoles unsubstituted on the nitrogen ($R^2$=H), and 29% for N-methyloxindole ($R^2$=Me).

As well as the very low yields, the disadvantages of the described process are also the use of strong bases such as sodium hydride, which lead to the formation of equimolar amounts of elemental hydrogen, which are difficult to handle industrially.

Consequently, the described process is not a viable solution for the industrial scale.

In the process, described in US 2004/116388 for the compound with the number 380, for the preparation of substituted 3-triazinyloxindoles, only 0.4 equivalents of the triazine component are used per equivalent of the oxindole component. Based on the oxindole component, this can lead merely to a maximum theoretical yield of 40%. An increase in the yield can be achieved through the use of an excess of oxindole. Since the oxindole component can, depending on the substitution pattern, be the somewhat more valuable starting material, this reaction procedure using a 2.5-fold excess of oxindole on an industrial scale is to be regarded as disadvantageous.

It has already been indicated that the reaction conditions for the exchange of the hydrogen in the 3 position of oxindoles for aliphatic, aromatic and heteroaromatic substituents had to be established in each case independently of one another because the type of substituents to be introduced can heavily influence the reaction.

The same appears to apply in turn to the further branching, i.e. the further substitution of these substituents, in particular to the further substitution of the heteroaromatic substituents.

Thus, the prior art describes no industrially suitable synthesis of 3-triazinyloxindoles which carry alkyl or alkoxy substituents on the triazine ring.

The use of the hitherto known preparation processes in the synthesis of 3-triazinyloxindoles which carry alkyl or alkoxy substituents on the triazine ring does not produce satisfactory results on an industrial scale.

For comparison purposes, the conditions, described in the document US 2004/116388, in the reaction of 7-fluoro-1,3-dihydro-2H-indol-2-one (example 1 Variant F), or 1,3-dihydro-2H-indol-2-one (Example 2 Variant B) with 2-chloro-4,6-dimethoxy-1,3,5-triazine were used.

In this connection, it was found that the yields achieved, in each case based on the oxindole component, are only 39% (Example 1 Variant F), or only 34% (Example 2 Variant B). If these conditions are used in the reaction of the starting materials in an industrially advantageous ratio, namely 1 equivalent of the oxindole component with 1.2 equivalents of the triazine component, then the yields achieved are 39% (Example 1 Variant G) or 30% (Example 2 Variant C).

In Organic Letters (2010) 2306-2309, in the arylation reactions described in Table 4, the starting material used in each case is 3-phenyloxindole, i.e. an oxindole which carries a phenyl substituent in the 3 position. This 3-phenyloxindole is arylated with electron-poor chlorobenzene derivatives and 5-halooxazoles in the presence of caesium carbonate in the 3 position.

As is known, the acidity of methyl groups or methylene groups is usually greatly increased by exchanging a hydrogen substituent for a phenyl substituent. This leads to a reduced pKa value of the remaining hydrogen substituent(s) on methyl group or methylene group by several orders of magnitude.

In a series of publications, corresponding examples can be found in which pKa values of organic or inorganic compounds in water or in organic solvents such as dimethyl sulfoxide are described. The pKa values in organic solvents were either measured directly or extrapolated by means of other methods. For example, in Acc. Chem. Res. 1988, 21, 456 in Table II, for 4-methylpyridine, a pKa value of 35 (extrapolated for DMSO) and for 4-benzylpyridine a pKa value of 26.7 (in DMSO) is given. Likewise in Acc. Chem. Res. 1988, 21, 456 in Table II, for (methylsulfanyl)benzene, a pKa value of 42 (extrapolated for DMSO) is given, for (benzylsulfanyl)benzene, a pKa value of 30.8 (in DMSO) is given, and for diphenylmethyl phenylsulfide, a pKa value of 26.8 (in DMSO) is given. For oxindole, in Acc. Chem. Res. 1988, 21, 456 in Table II, a pKa value of 18.2 (in DMSO) is given.

From the examples given, the increase in acidity of methyl groups or methylene groups by several orders of magnitude as a result of exchanging a hydrogen substituent for a phenylsubstituent becomes very evident.

In the examples of the present application, the starting materials used were only oxindoles which carry two hydrogen atoms in the 3 position. In Organic Letters (2010) 2306-2309, by contrast, 3-phenyloxindoles are used as starting materials. The starting materials therefore differ in their acidity. Oxindoles which carry two hydrogen atoms in the 3 position are less acidic than the 3-phenyloxindole used in Organic Letters (2010) 2306-2309 in the reactions of Table 4.

It is therefore not surprising that in the literature examples in which arylation reactions on oxindoles unsubstituted in the 3 position are described, strong bases such as sodium hydride are used. The fact that also for oxindoles which carry a substituent in the 3 position which reduces the acidity in non-aqueous solvents by several orders of magnitude, relatively weak bases such as caesium carbonate can be used for the deprotonation was to be expected by the person skilled in the art and was confirmed in Organic Letters (2010) 2306-2309.

However, it is surprising to the person skilled in the art that, according to the teaching of the invention, an arylation reaction on oxindoles unsubstituted in the 3 position (oxindoles which have two hydrogens in the 3 position) is possible, contrary to expectations, even with relatively weak bases such as potassium carbonate or sodium hydroxide in good yields.

In order to test the applicability of the conditions described in Organic Letters (2010) 2306 (Supplement page S-12 General Procedure) for the arylation of 3-aryloxindoles with electron-poor chlorobenzene derivatives and 5-halooxazoles (Table 4 in Organic Letters (2010) 2306) also when using chlorotriazines, 3-phenyl-1,3-dihydro-2H-indol-2-one was reacted with 2-chloro-4,6-dimethoxy-1,3,5-triazine in the presence of caesium carbonate in N,N-dimethylformamide (see Example 10). Since the reaction proceeded very rapidly even at room temperature, an elevated temperature and extended reaction time were dispensed with. The product present in the reaction mixture was purified by column chromatography. Structural elucidation by means of 2D-NMR demonstrates that the product obtained, however, is not the desired product arylated in the 3 position (3-(4,6-dimethoxy-1,3,5-triazin-2-yl)-3-phenyl-1,3-dihydro-2H-indol-2-one), but the O-arylated product (2-[(4,6-dimethyoxy-1,3,5-triazin-2-yl)oxy]-3-phenyl-1H-indole).

Afterwards, again for comparison purposes, the conditions for the arylation described in Organic Letters (2010) 2306 (Supplement page S-12 General Procedure) were likewise applied while using chlorotriazines, and specifically for the arylation of an oxindole unsubstituted in the 3 position. For this purpose, 7-fluoro-1,3-dihydro-2H-indol-2-one was reacted with 2-chloro-4,6-dimethoxy-1,3,5-triazine in the presence of caesium carbonate in N,N-dimethylformamide (Example 1 variant H). However, the title compound arylated in the 3 position with only 22% yield is obtained as reaction product. As main products, polyarylated products were obtained in the isolated solid and also in the concentrated mother liquor. It was also shown, by means of HPLC analysis, that the oxindole used as starting material had not completely fully reacted.

Consequently, the process described in Organic Letters (2010) 2306 (Supplement page S-12 General Procedure) is not suitable for producing 3-triazinyloxindoles on an industrial scale, at least when 2-chloro-4,6-dimethoxy-1,3,5-triazine is used as arylating reagent.

SUMMARY

Against this background, the object of the invention consists in the provision of an improved process which permits, on an industrial scale, a preparation of 3-triazinyloxindoles that is simplified compared to the known processes, coupled with improved overall yield.

Surprisingly, it has now been found that the relatively weak bases potassium carbonate or sodium carbonate, and also lithium hydroxide, sodium hydroxide, potassium hydroxide, barium hydroxide or tert-alkylammonium hydroxide, and also potassium phosphate ($K_3PO_4$), $K_2HPO_4$ or sodium phosphate or mixtures consisting of at least two of the aforementioned bases, are suitable for achieving the object.

The specified bases have the advantage that they are suitable for use on an industrial scale since they cannot be decomposed particularly in the presence of water, and also do not produce equimolar amounts of hydrogen and at the same time lead to a significantly improved overall yield.

The object is thus achieved by a process for the preparation of compounds of formula (3)

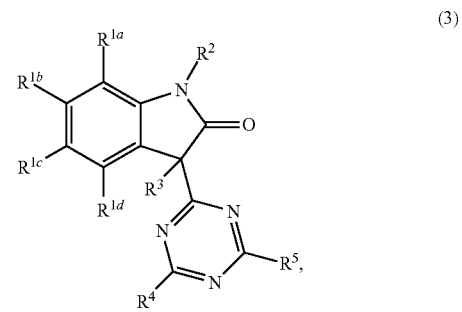

(3)

in which
$R^{1a}$ to $R^{1d}$, independently of one another, are selected from the group consisting of hydrogen, fluorine, chlorine, bromine, iodine, and also from ($C_1$-$C_6$)-alkyl, where the alkyl radical is branched or unbranched and is unsubstituted or is substituted by one or more substituents selected from the group consisting of fluorine, chlorine, ($C_1$-$C_4$)-alkoxy or ($C_3$-$C_7$)-cycloalkyl, ($C_3$-$C_7$)-cycloalkyl, where the cycloalkyl radical is unsubstituted or is substituted by one or more substituents selected from the group consisting of fluorine, chlorine, ($C_1$-$C_4$)-alkyl or ($C_3$-$C_7$)-cycloalkyl or ($C_1$-$C_4$)-alkoxy, ($C_1$-$C_6$)-alkoxy, where the alkoxy radical is branched or unbranched and is unsubstituted or is substituted by one or more substituents selected from the group consisting of fluorine, chlorine, ($C_1$-$C_4$)-alkoxy or ($C_3$-$C_7$)-cycloalkyl, ($C_3$-$C_7$)-cycloalkoxy, where the cycloalkoxy radical is unsubstituted or is substituted by one or more substituents selected from the group consisting of fluorine, chlorine, ($C_1$-$C_4$)-alkyl or ($C_1$-$C_4$)-alkoxy, ($C_1$-$C_6$)-alkylthio, where the alkylthio radical is branched or unbranched and is unsubstituted or is substituted by one or more substituents selected from the group consisting of fluorine, chlorine, ($C_1$-$C_4$)-alkyl or ($C_1$-$C_4$)-alkoxy, ($C_3$-$C_7$)-cycloalkylthio, where the cycloalkylthio radical is unsubstituted or is substituted by one or more substituents selected from the group consisting of fluorine, chlorine, ($C_1$-$C_4$)-alkyl or ($C_1$-$C_4$)-alkoxy, and phenyl or 1-naphthyl or 2-naphthyl or a five- or six-membered heteroaromatic ring having 1 to 2 heteroatoms, where the heteroatoms, independently of one another, are selected from the group consisting of O or N and where the aryl or heteroaryl radical is unsubstituted or is substituted by one or more substituents selected from the group consisting of fluorine, chlorine, bromine, iodine, ($C_1$-$C_4$)-alkyl, ($C_1$-$C_4$)-alkoxy or ($C_3$-$C_7$)-cycloalkyl or ($C_1$-$C_4$)-alkylthio, and $R^2$ is
hydrogen,
($C_1$-$C_6$)-alkyl, where the alkyl radical is unsubstituted or is substituted by one or more substituents selected from the group consisting of fluorine, chlorine, ($C_1$-$C_4$)-alkoxy or ($C_3$-$C_7$)-cycloalkyl, or benzyl, where the benzyl is unsubstituted or is substituted by one or more substituents selected from the group consisting of fluorine, chlorine, bromine, iodine, nitro, ($C_1$-$C_4$)-alkyl, ($C_1$-$C_4$)-alkoxy or ($C_3$-$C_7$)-cycloalkyl or ($C_1$-$C_4$)-alkylthio and also from $COOR^a$, in which $R^a$ is a ($C_1$-$C_4$)-alkyl, and —$CONR^{b'}R^{b''}$ or —$CONHR^{b''}$, in which $R^{b'}$ and $R^{b''}$ are each independently of one another a ($C_1$-$C_4$)-alkyl, where in each case two substituents on the N atom together optionally form an unsubstituted or substituted ring, $R^3$ is
  hydrogen,
$R^4$ and $R^5$, independently of one another, are in each case
  hydrogen,
  ($C_1$-$C_6$)-alkyl, where the alkyl radical is unsubstituted or is substituted by one or more substituents selected from the group consisting of fluorine, chlorine, ($C_1$-$C_4$)-alkoxy or ($C_3$-$C_7$)-cycloalkyl,
  ($C_1$-$C_6$)-alkoxy, where the alkoxy radical is branched or unbranched and is unsubstituted or is substituted by one or more substituents selected from the group consisting of fluorine, chlorine, ($C_1$-$C_4$)-alkoxy or ($C_3$-$C_7$)-cycloalkyl,
where an oxindole (1)

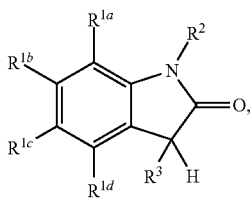

(1)

in which
$R^{1a}$ to $R^{1d}$ and $R^2$ and $R^3$ are as defined in formula (3), is reacted in a solvent with a triazine (2)

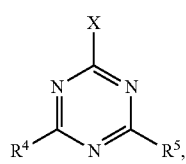

(2)

in which
$R^4$ and $R^5$ are as defined in formula (3), and
X, as leaving group, is Cl, Br, I, alkoxy, alkylsulfonyl, (alkylsulfonyl)oxy, haloalkylsulfonyl, phenylsulfonyl or toluene-4-sulfonyl,
which comprises carrying out the reaction in the presence of
  potassium carbonate or sodium carbonate,
  lithium hydroxide, sodium hydroxide, potassium hydroxide, barium hydroxide or tert-alkylammonium hydroxide,
  potassium phosphate ($K_3PO_4$), potassium hydrogenphosphate ($K_2HPO_4$) or sodium phosphate or
in a mixture comprising at least two of the aforementioned bases.

DETAILED DESCRIPTION OF A PREFERRED EMBODIMENT

Wherever reference is made in this application to an "oxindole", one of the compounds encompassed by formula (1) is intended. The oxindoles (1) used as starting materials

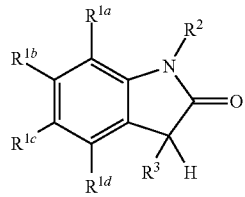

(1)

in which the radicals $R^{1a}$ to $R^{1d}$, $R^2$ and $R^3$ are as defined above, are known or can be prepared using the processes known to the person skilled in the art. Wherever reference is made in this application to a "triazine" or a "triazine component", one of the compounds encompassed by formula (2) is intended. The triazines (2) likewise used as starting materials

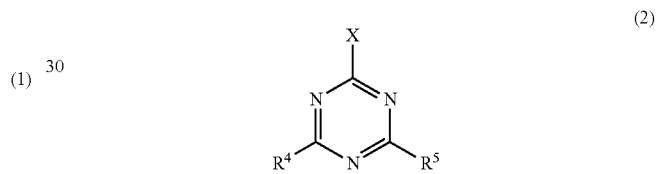

(2)

in which $R^4$, $R^5$ and X are as defined above, are likewise known or can be prepared using processes known to the person skilled in the art.

As regards the compounds according to the invention, the terms used above and below are explained in summary. These are familiar to the person skilled in the art and have in particular the meanings explained below:

The term "halogen" means, for example, fluorine, chlorine, bromine or iodine. If the term is used for a radical, then "halogen" means for example a fluorine, chlorine, bromine or iodine atom.

Alkyl means a straight-chain or branched open-chain, saturated hydrocarbon radical.

The expression "($C_1$-$C_4$)-alkyl" is short-hand for alkyl having one to 4 carbon atoms corresponding to the stated range for carbon atoms, i.e. encompasses the radicals methyl, ethyl, 1-propyl, 2-propyl, 1-butyl, 2-butyl, 2-methylpropyl or tert-butyl. General alkyl radicals with a larger stated range of carbon atoms, e.g. "($C_1$-$C_6$)-alkyl", accordingly also encompass straight-chain or branched alkyl radicals having a larger number of carbon atoms, i.e. according to the example also the alkyl radicals having 5 and 6 carbon atoms.

Cycloalkyl means a carbocyclic, saturated ring system having preferably 3-8 ring carbon atoms, e.g. cyclopropyl, cyclobutyl, cyclopentyl or cyclohexyl. In the case of optionally substituted cycloalkyl, cyclic systems with substituents are encompassed, in which case also substituents with a double bond on the cycloalkyl radical, e.g. an alkylidene group such as methylidene, are encompassed.

In the case of optionally substituted cycloalkyl, also polycyclic aliphatic systems are encompassed, such as, for example, bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), adamantan-1-yl and adamantan-2-yl.

In the case of substituted cycloalkyl, also spirocyclic aliphatic systems are encompassed, such as, for example spiro[2.2]pent-1-yl, spiro[2.3]hex-1-yl, spiro[2.3]hex-4-yl, 3-spiro[2.3]hex-5-yl.

Aryl means a mono-, bi- or polycyclic aromatic system having preferably 6 to 14, in particular 6 to 10, ring carbon atoms, for example phenyl, naphthyl, anthryl, phenanthrenyl, and the like, preferably phenyl.

The term "optionally substituted aryl" also encompasses polycyclic systems, such as tetrahydronaphthyl, indenyl, indanyl, fluorenyl, biphenylyl, the bonding site being on the aromatic system.

From the point of view of systematics, aryl is usually also encompassed by the term "optionally substituted phenyl".

Alkoxy means an alkyl radical bonded via an oxygen atom, alkenyloxy means an alkenyl radical bonded via an oxygen atom, alkynyloxy means an alkynyloxy radical bonded via an oxygen, cycloalkyloxy means a cycloalkyl radical bonded via an oxygen atom and cycloalkenyloxy means a cycloalkenyl radical bonded via an oxygen atom.

Alkylthio means an alkyl radical bonded via a sulfur atom, alkenylthio means an alkenyl radical bonded via a sulfur atom, alkynylthio means an alkynyl radical bonded via a sulfur atom, cycloalkylthio means a cycloalkyl radical bonded via a sulfur atom and cycloalkenylthio means a cycloalkenyl radical bonded via a sulfur atom.

Haloalkyl, haloalkenyl and haloalkynyl mean alkyl, alkenyl or alkynyl, respectively, partially or completely substituted by identical or different halogen atoms, e.g. monohaloalkyl, such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2F$, $CH_2CHFCl$, $CHCl_2$, $CF_2CF_2H$, $CH_2CF_3$; haloalkoxy is e.g. $OCF_3$, $OCHF_2$, $OCH_2F$, $OCF_2CF_3$, $OCH_2CF_3$ and $OCH_2CH_2Cl$; the same applies to haloalkenyl and other radicals substituted by halogen.

Unless defined otherwise, the definition "is substituted with one or more radicals" means, independently of one another, one or more identical or different radicals where two or more radicals on a cycle as parent body are able to form one or more rings.

Substituted radicals, such as a substituted alkyl, cycloalkyl, cycloalkenyl, aryl, phenyl, benzyl, heterocyclyl and heteroaryl radical, are, for example, a substituted radical derived from the unsubstituted parent body, where the substituents are, for example, one or more, preferably 1, 2 or 3 radicals from the group halogen, alkoxy, alkylthio, hydroxy, amino, nitro, carboxy or a group equivalent to the carboxy group, cyano, isocyano, azido, alkoxycarbonyl, alkylcarbonyl, formyl, carbamoyl, mono- and dialkylaminocarbonyl, substituted amino, such as acylamino, mono- and dialkylamino, trialkylsilyl and optionally substituted cycloalkyl, optionally substituted aryl, optionally substituted heterocyclyl, where each of the last-mentioned cyclic groups can also be bonded via heteroatoms or divalent functional groups as in the case of the specified alkyl radicals, and alkylsulfinyl, where both enantiomers of the alkylsulfinyl group are encompassed, alkylsulfonyl, alkylphosphinyl, alkylphosphonyl and, in the case of cyclic radicals (="cyclic parent body"), also alkyl, haloalkyl, alkylthioalkyl, alkoxyalkyl, optionally substituted mono- and dialkylaminoalkyl and hydroxyalkyl.

In the term "substituted radicals" such as substituted alkyl etc., as well as the specified saturated hydrocarbon-containing radicals, corresponding unsaturated aliphatic and aromatic radicals are included as substituents, such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and dialkenylaminocarbonyl, mono- and dialkynylaminocarbonyl, mono- and dialkenylamino, mono- and dialkynylamino, trialkenylsilyl, trialkynylsilyl, optionally substituted cycloalkenyl, optionally substituted cycloalkynyl, phenyl, phenoxy etc. In the case of substituted cyclic radicals with aliphatic moieties in the ring, also encompassed are cyclic systems with those substituents which are bonded to a double bond on the ring, e.g. are substituted with an alkylidene group such as methylidene or ethylidene or an oxo group, imino group or substituted imino group.

The unsubstituted or substituted radicals in each case can be branched or unbranched. Thus, for example, a radical referred to as "$C_4$-alkyl" encompasses, as well as the unbranched butyl radical, all further $C_4$ isomers, including tert-butyl.

If two or more radicals form one or more rings, then these may be carbocyclic, heterocyclic, saturated, partially saturated, unsaturated, for example also aromatic and optionally further substituted. The fused rings are preferably 5- or 6-membered rings, particular preference being given to benzo-condensed cycles.

The core of the process according to the invention consists in the reaction of the starting materials of formula (1) and (2) in the presence of bases which are characterized in that they do not decompose in the presence of water and, moreover, do not release hydrogen ($H_2$) during the reaction.

Some very strong to medium-strength bases, such as, e.g. sodium hydride (NaH), react in water with decomposition and are therefore unsuitable for industrial application. Bases having these disadvantages can only be handled safely on a laboratory scale. For industrial application, strong bases, such as NaH, are therefore unsuitable.

In the reaction according to the invention the base used is preferably potassium carbonate or sodium carbonate, and also
lithium hydroxide, sodium hydroxide, potassium hydroxide, barium hydroxide or tert-alkylammonium hydroxide, and also
potassium phosphate ($K_3PO_4$), $K_2HPO_4$ or sodium phosphate, or mixtures of at least two of the aforementioned bases.

Compared with strong bases, such as e.g. sodium hydride, the specified carbonates, hydroxides and phosphates have the essential advantage that they are industrially more suitable since, in the case of their use, no equimolar amounts of hydrogen are formed and the specified weaker bases also do not decompose in the presence of water.

Particularly preferred bases are potassium carbonate, sodium carbonate, sodium hydroxide, potassium hydroxide or an at least two-component mixture consisting of at least one of the two carbonates: potassium carbonate and sodium carbonate, and also of at least one of the two hydroxides: potassium hydroxide or sodium hydroxide.

The four particularly preferred two-component mixtures thus relate to the mixtures consisting of potassium carbonate and potassium hydroxide, potassium carbonate and sodium hydroxide, sodium carbonate and potassium hydroxide, and also the mixture consisting of potassium carbonate and sodium hydroxide.

In addition, further mixtures which in each case comprise more than two of the bases specified as being particularly preferred for the reaction are naturally conceivable.

Since the bases used according to the invention comprise water, and/or can generate it or release it, but triazines (2) slightly hydrolyze in the presence of water, it has to be regarded as surprising that the bases used according to the invention could prove suitable at all for achieving the object.

In a preferred embodiment of the process according to the invention, the radicals $R^{1a}$ to $R^{1d}$ in the compounds of formulae (3) and (1) are selected, independently of one another, from the group consisting of hydrogen, fluorine, chlorine, bromine, iodine, and also from ($C_1$-$C_6$)-alkyl, where the alkyl radical is branched or unbranched and is unsubstituted or is substituted by one or more substituents selected from the group consisting of fluorine and chlorine, and ($C_3$-$C_7$)-cycloalkyl, where the cycloalkyl radical is unsubstituted or is substituted by one or more substituents selected from the group consisting of fluorine, chlorine, ($C_1$-$C_4$)-alkyl or ($C_3$-$C_7$)-cycloalkyl or ($C_1$-$C_4$)-alkoxy.

In a particularly preferred embodiment, the radicals $R^{1a}$ to $R^{1d}$ in the compounds of formulae (3) and (1) are selected, independently of one another, from the group consisting of fluorine, chlorine and trifluoromethyl ($CF_3$), trifluoromethoxy (O—$CF_3$) and methoxy (O-Me).

In a very particularly preferred embodiment, the radical $R^{1a}$ is fluorine or chlorine, i.e. the compounds of formulae (3) and (1) are substituted in the 7 position by fluorine (7-fluoro) or chlorine (7-chloro).

Very particular preference is likewise given to compounds of formulae (3) and (1) which are substituted in the 5 position by fluorine (5-fluoro), i.e. the radical $R^{1c}$ is fluorine (see Example 5).

Furthermore, very particular preference is also given to compounds of formulae (3) and (1) which are substituted in the 7 position by fluorine (7-fluoro) and at the same time in the 5 position by fluorine (5-fluoro), i.e. the radicals $R^{1a}$ and $R^{1c}$ are fluorine (see Example 3).

In a further particularly preferred embodiment, the radical $R^2$ in formulae (3) and (1) is
hydrogen, or is in each case
unsubstituted methyl, ethyl and benzyl.

In a very particularly preferred embodiment, the nitrogen in the 1 position of the compounds of formulae (3) and (1) is unsubstituted, i.e. the radical $R^2$ is hydrogen.

Within the scope of the invention, it is preferred that the reaction mixture from which the product of formula (3) where $R^3$=H can be obtained, is rendered acidic by adding acid or a mixture of acids, in particular hydrochloric acid, sulfuric acid, acetic acid or formic acid, in a technically relevant concentration, then the organic solvent is completely or partially distilled off and the residue is filtered. The solid product obtained in this way can be washed with suitable solvents.

Furthermore, it is particularly preferred that the reaction mixture from which the product of formula (3) where $R^3$=H can be obtained, is rendered acidic by adding hydrochloric acid or sulfuric acid of a technically relevant concentration, acetic acid or formic acid, and additionally a further organic solvent is added and the residue is filtered. The solid product obtained in this way can be washed with suitable solvents.

It is within the scope of the invention that, before or during the acidification, a suitable amount of antifoam is added to the reaction mixture which comprises products of formula (3) in order to reduce undesired foaming of the reaction mixture.

In a particularly preferred embodiment, the radicals $R^4$ and $R^5$ in formulae (2) and (3) are, independently of one another, in each case unsubstituted ($C_1$-$C_4$)-alkyl and unsubstituted ($C_1$-$C_4$)-alkoxy.

Very particular preference is given to compounds of formulae (2) and (3) in which the radicals $R^4$ and $R^5$ are, independently of one another, in each case methoxy, ethoxy, methyl, ethyl.

In a particularly preferred embodiment, the leaving group X is a chlorine.

An important aspect relates to the selection of the solvent in which the reaction is carried out. The reaction can be carried out in
a polar or
a nonpolar solvent, or in
a mixture of a polar or nonpolar solvent.
Nonpolar solvents which can be used are
haloalkanes, in particular dichloromethane or dichloroethane; or
aromatics, in particular toluene, xylene or chlorobenzene.
Polar organic solvents which can be used are
ketones, in particular acetone, butanone, 2-methylbutanone;
nitriles, in particular acetonitrile, butyronitrile, isobutylnitrile;
amides, in particular N,N-dimethylformamide, N,N-dimethylacetamide, formamide, N-methylformamide, N-methylpyrrolidone;
sulfoxides and sulfones, for example dimethyl sulfoxide, dimethyl sulphones, sulfolane;
ethers, in particular dioxane, 2-methyltetrahydrofuran, methyl cyclopentyl ether, tert-butyl methyl ether or tetrahydrofuran; or
esters, in particular ethyl acetate, n-butyl acetate or isopropyl acetate.

The specified polar solvents can be used either on their own or in mixtures with other solvents, preferably with further polar organic solvents or with water. In this connection, it is not excluded that the reaction also takes place in water as the sole solvent.

Particular preference is given to carrying out the process without using water as solvent.

The process according to the invention for the preparation of compounds of formula (3) is based on the fact that the oxindole (1 equivalent) is reacted in a suitable solvent with the triazine component and the base. In this connection, the triazine component is preferably used in excess (1.1 to 1.4 equivalents, preferably 1.1 to 1.25 equivalents).

The base is used in equimolar amount or in excess. If $R^2$=H, the base is used with 2 to 3 equivalents, preferably with 2.2 to 2.6 equivalents.

All reactants can be added to the reaction mixture either in pure form or premixed with one another or dissolved or suspended in a solvent or a solvent mixture.

For good product yields, it has been found that it may be advantageous to firstly react the oxindole with the base (total amount or part amount) in a suitable solvent, and then to add the triazine component and, if appropriate, a further amount of the same or of a different base or a mixture of different bases in one or more portions.

Another addition variant consists in initially introducing the oxindole and the triazine component in a suitable solvent and adding the base, or the mixture of different bases, in portions.

The addition of the reactants can take place in one or more portions over a period of up to 24 hours, preferably up to 6 hours, in particular 0.05 to 6 hours.

The reaction temperature is in the range from −20° C. to 150° C., preferably in the range from −10° C. to 90° C.

If appropriate, the reaction can be carried out under pressure.

In the course of the reaction, further solvent can be added in order to permit better mixing of the reactants.

Depending on the reaction conditions used, the after-stirring time following addition of all reactants is in the range up to 48 hours, preferably 0.05 to 24 hours.

Work-up and isolation of the desired product of formula (3) can take place in various ways, for example irrespective of which solvent is used or whether the product is a solid or a liquid.

The invention also provides the compounds of formula (3), (3)

which are obtainable for example by the process according to the invention described above, and salts thereof (3"), (3")

in which, in each case
$R^{1a}$ to $R^{1d}$, independently of one another, are selected from the group consisting of hydrogen, fluorine, chlorine, bromine, iodine, and also from ($C_1$-$C_6$)-alkyl, where the alkyl radical is branched or unbranched and is unsubstituted or is substituted by one or more substituents selected from the group consisting of fluorine, chlorine, ($C_1$-$C_4$)-alkoxy or ($C_3$-$C_7$)-cycloalkyl, ($C_3$-$C_7$)-cycloalkyl, where the cycloalkyl radical is unsubstituted or is substituted by one or more substituents selected from the group consisting of fluorine, chlorine, ($C_1$-$C_4$)-alkyl or ($C_3$-$C_7$)-cycloalkyl or ($C_1$-$C_4$)-alkoxy, ($C_1$-$C_6$)-alkoxy, where the alkoxy radical is branched or unbranched and is unsubstituted or is substituted by one or more substituents selected from the group consisting of fluorine, chlorine, ($C_1$-$C_4$)-alkoxy or ($C_3$-$C_7$)-cycloalkyl, ($C_3$-$C_7$)-cycloalkoxy, where the cycloalkoxy radical is unsubstituted or is substituted by one or more substituents selected from the group consisting of fluorine, chlorine, ($C_1$-$C_4$)-alkyl or ($C_1$-$C_4$)-alkoxy, ($C_1$-$C_6$)-alkylthio, where the alkylthio radical is branched or unbranched and is unsubstituted or is substituted by one or more substituents selected from the group consisting of fluorine, chlorine, ($C_1$-$C_4$)-alkyl or ($C_1$-$C_4$)-alkoxy, ($C_3$-$C_7$)-cycloalkylthio, where the cycloalkylthio radical is unsubstituted or is substituted by one or more substituents selected from the group consisting of fluorine, chlorine, ($C_1$-$C_4$)-alkyl or ($C_1$-$C_4$)-alkoxy, and phenyl or 1-naphthyl or 2-naphthyl or a five- or six-membered heteroaromatic ring having 1 to 2 heteroatoms, where the heteroatoms, independently of one another, are selected from the group consisting of O or N and where the aryl or heteroaryl radical is unsubstituted or is substituted by one or more substituents selected from the group consisting of fluorine, chlorine, bromine, iodine, ($C_1$-$C_4$)-alkyl, ($C_1$-$C_4$)-alkoxy or ($C_3$-$C_7$)-cycloalkyl or ($C_1$-$C_4$)-alkylthio, and $R^2$ is
hydrogen,
($C_1$-$C_6$)-alkyl, where the alkyl radical is branched or unbranched and is unsubstituted or is substituted by one or more substituents selected from the group consisting of fluorine, chlorine, ($C_1$-$C_4$)-alkoxy or ($C_3$-$C_7$)-cycloalkyl, or
benzyl, where the benzyl is unsubstituted or is substituted by one or more substituents selected from the group consisting of fluorine, chlorine, bromine, iodine, nitro, ($C_1$-$C_4$)-alkyl, ($C_1$-$C_4$)-alkoxy or ($C_3$-$C_7$)-cycloalkyl or ($C_1$-$C_4$)-alkylthio and also from $COOR^a$, in which $R^a$ is a ($C_1$-$C_4$)-alkyl, and —$CONR^{b'}R^{b''}$ or —$CONHR^{b''}$, in which $R^{b'}$ and $R^{b''}$ are each independently of one another a ($C_1$-$C_4$)-alkyl, where in each case two substituents on the N atom together optionally form an unsubstituted or substituted ring, $R^3$ is
hydrogen,
$R^4$ and $R^5$, independently of one another, are in each case hydrogen,
($C_1$-$C_6$)-alkyl, where the alkyl radical is unsubstituted or is substituted by one or more substituents selected from the group consisting of fluorine, chlorine, ($C_1$-$C_4$)-alkoxy or ($C_3$-$C_7$)-cycloalkyl,
($C_1$-$C_6$)-alkoxy, where the alkoxy radical is branched or unbranched and is unsubstituted or is substituted by one or more substituents selected from the group consisting of fluorine, chlorine, ($C_1$-$C_4$)-alkoxy or ($C_3$-$C_7$)-cycloalkyl, where, in the salts of formula (3"),
M is Li, Na, K, $N(R^c)_4$, where $R^c$=H or $C_1$-$C_6$-alkyl, Cs, Ba, Mg, Ca and Zn, and the number of counterions $M^+$ is governed by the particular charge, such that an overall neutral compound of formula (3") is formed.

The formulae (3) and (3"), if applicable, also include all stereoisomers, tautomers and/or polymorphous forms, and also salts thereof.

Particular preference is given to compounds of the formulae (3) in which $R^3$ is H or methyl.

Compounds of the formulae (3) in which $R^3$ is H are most preferred.

Compounds of the formulae (3) and (3") and also the compounds of formula (3) prepared by the process according to the invention are suitable as intermediates for producing fine chemicals and active ingredients from agriculture.

Compounds of formula (3) and (3") are triazinyl-substituted oxindoles. In scheme 3 below, triazinyl-substituted oxindoles are referred to by formula (5-1).

Scheme 3 shows a novel multistage synthesis process, according to which, starting from a 3-(alkylsulfanyl)-1,3-dihydro-2H-indol-2-one of formula (7-1) in an overall five-stage reaction, an N-alkyl-N-[2-(1,3,5-triazine-2-ylcarbonyl)phenyl]alkanesulfonamide of formula (4-1) can be prepared, the herbicidal activity (see WO 2007/031208 A2) and fungicidal activity (see WO 2006/008159 A1) of which has already been known for a relatively long time.

Scheme 3: multistage process for the preparation of in particular herbicidal N-alkyl-N-[2-(1,3,5-triazine-2-ylcarbonyl)phenyl]alkanesulfonamides (4-1) suitable for crop protection.

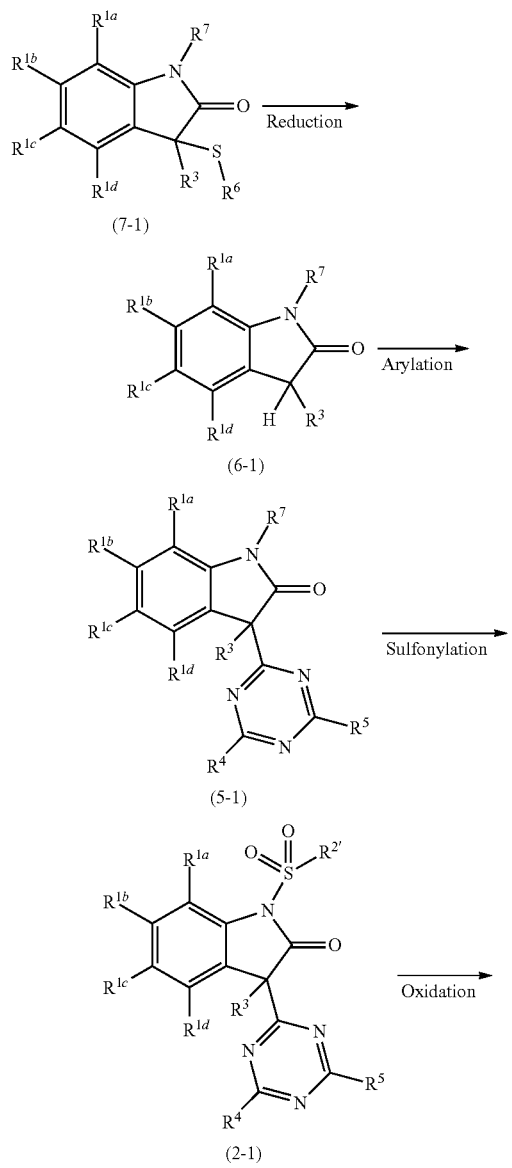

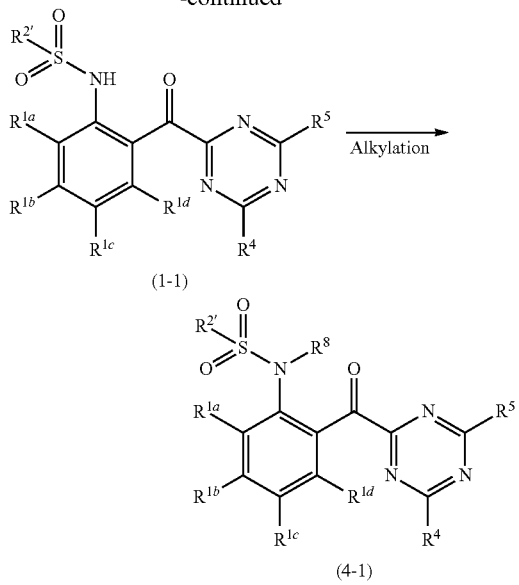

The multistage process for the preparation of N-alkyl-N-[2-(1,3,5-triazin-2-ylcarbonyl)phenyl]alkanesulfonamides (4-1) consists of the following part steps:

Reduction of substituted or unsubstituted 3-(alkylsulfanyl)-1,3-dihydro-2H-indol-2-ones (7-1) to give substituted or unsubstituted 1,3-dihydro-2H-indol-2-ones (6-1). This process is possible on an industrial scale and is described in the patent application with the application number EP 10162381.7.

Arylation of substituted or unsubstituted 1,3-dihydro-2H-indol-2-ones (6-1) to give triazinyl-substituted oxindoles (5-1). This process is possible on an industrial scale and is described in the present patent application.

Sulfonylation of triazinyl-substituted oxindoles (5-1) to give N-sulfonyl-substituted 3-triazinyloxindoles (2-1). This process is possible on an industrial scale and is described in the patent application with the application number EP 111598751.

Oxidative ring-opening of N-sulfonyl-substituted 3-triazinyloxindoles (2-1) to give 2-(triazinylcarbonyl)sulfonanilides (1-1). This process is possible on an industrial scale and is described in the patent application with the application number DE 102011086382.6.

Alkylation of 2-(triazinylcarbonyl)sulfonanilides (1-1) to give N-alkyl-N-[2-(1,3,5-triazin-2-ylcarbonyl)phenyl]alkanesulfonamides (4-1). This process is described in the patent application with the application number WO 2006/008159.

The novel multistage process shown in scheme 3 is distinguished from the previously known processes for the preparation of N-alkyl-N-[2[(1,3,5-triazin-2-ylcarbonyl)phenyl]alkanesulfonamides (4-1) and 2-(triazinylcarbonyl)sulfonanilides (1-1) in that oxindole compounds are used as starting materials and/or as intermediates. This has the advantage that, compared to the previously known processes, it can be carried out on an industrial scale, and at the same time high yields can be attained.

The practicability of the process summarized in scheme 3 is disclosed in detail below. The reduction, which in scheme 3 concerns the first reaction step of the overall five-stage process has been treated below as independent preliminary stage B). The process A) described in detail below thus encompasses the steps of arylation, sulfonylation, oxidation and alkylation.

A) process for the preparation of N-alkyl-N-[2-(1,3,5-triazine-2-ylcarbonyl)phenyl]alkanesulfonamides of formula (4-1)

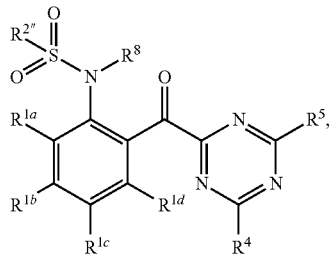

(4-1)

in which
$R^{1a}$ to $R^{1d}$, independently of one another, are selected from the group consisting of hydrogen, fluorine, chlorine, bromine, iodine, and also from
- $(C_1-C_6)$-alkyl, where the alkyl radical is unsubstituted or is substituted by one or more substituents selected from the group consisting of fluorine, chlorine, $(C_1-C_4)$-alkoxy or $(C_3-C_7)$-cycloalkyl,
- $(C_3-C_7)$-cycloalkyl, where the cycloalkyl radical is unsubstituted or is substituted by one or more substituents selected from the group consisting of fluorine, chlorine, $(C_1-C_4)$-alkyl or $(C_3-C_7)$-cycloalkyl or $(C_1-C_4)$-alkoxy,
- $(C_1-C_6)$-alkoxy, where the alkoxy radical is unsubstituted or is substituted by one or more substituents selected from the group consisting of fluorine, chlorine, $(C_1-C_4)$-alkoxy or $(C_3-C_7)$-cycloalkyl,
- $(C_3-C_7)$-cycloalkoxy, where the cycloalkoxy radical is unsubstituted or is substituted by one or more substituents selected from the group consisting of fluorine, chlorine, $(C_1-C_4)$-alkyl or $(C_1-C_4)$-alkoxy,
- $(C_1-C_6)$-alkylthio, where the alkylthio radical is unsubstituted or is substituted by one or more substituents selected from the group consisting of fluorine, chlorine, $(C_1-C_4)$-alkyl or $(C_1-C_4)$-alkoxy,
- $(C_3-C_7)$-cycloalkylthio, where the cycloalkylthio radical is unsubstituted or is substituted by one or more substituents selected from the group consisting of fluorine, chlorine, $(C_1-C_4)$-alkyl or $(C_1-C_4)$-alkoxy, and phenyl or 1-naphthyl or 2-naphthyl or a five- or six-membered heteroaromatic ring having 1 to 2 heteroatoms, where the heteroatoms, independently of one another, are selected from the group consisting of O or N and where the aryl or heteroaryl radical is unsubstituted or is substituted by one or more substituents selected from the group consisting of fluorine, chlorine, bromine, iodine, $(C_1-C_4)$-alkyl, $(C_1-C_4)$-alkoxy or $(C_3-C_7)$-cycloalkyl or $(C_1-C_4)$-alkylthio, and
$R^{2''}$ is
- $(C_1-C_6)$-alkyl, where the alkyl radical is unsubstituted or is completely or partially substituted with fluorine, or
- $(C_3-C_7)$-cycloalkyl, where the cycloalkyl radical is unsubstituted or is completely or partially substituted with fluorine, $R^4$ and $R^5$, independently of one another, are in each case hydrogen,

- $(C_1-C_6)$-alkyl, where the alkyl radical is unsubstituted or is substituted by one or more substituents selected from the group consisting of fluorine, chlorine, $(C_1-C_4)$-alkoxy or $(C_3-C_7)$-cycloalkyl,
- $(C_1-C_6)$-alkoxy, where the alkoxy radical is branched or unbranched and is unsubstituted or is substituted by one or more substituents selected from the group consisting of fluorine, chlorine, $(C_1-C_4)$-alkoxy or $(C_3-C_7)$-cycloalkyl, and
$R^8$ is
- $(C_1-C_6)$-alkyl, where the alkyl radical is unsubstituted or is completely or partially substituted with fluorine,
- $(C_1-C_6)$-cycloalkyl, $(C_1-C_6)$-alkenyl or $(C_1-C_6)$-alkoxylalkyl, where each of the specified radicals is unsubstituted or is completely or partially substituted with fluorine, where
a 1,3-dihydro-2H-indol-2-one of formula (6-1)

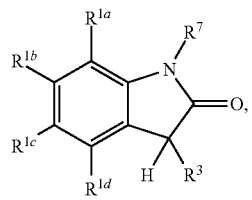

(6-1)

in which
$R^{1a}$ to $R^{1d}$ are as defined for formula (4-1),
$R^3$ is hydrogen, and
$R^7$ is hydrogen, is reacted in a
first step by
  arylation to give a triazinyl-substituted oxindole of formula (5-1)

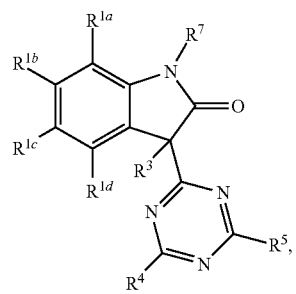

(5-1)

in which
$R^{1a}$ to $R^{1d}$ and $R^4$ and $R^5$ are as defined for formula (4-1) and $R^3$ and $R^7$ are as defined for formula (5-1), and the arylation products of formula (5-1) are reacted in a
second step by
  sulfonylation to give N-sulfonyl-substituted 3-triazinyloxindoles of formula (2-1)

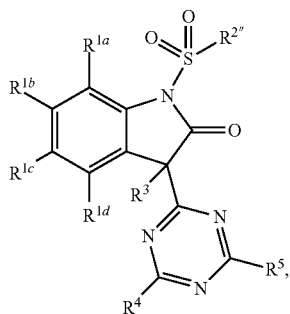

(2-1)

in which
R$^{1a}$ to R$^{1d}$, R$^{2''}$ and also R$^4$ and R$^5$ are as defined in formula (4-1), and R$^3$ is as defined for formula (5-1), and the solfonylation products of formula (2-1) are reacted in a third step by
oxidative ring opening to give a 2-(triazinylcarbonyl)sulfonanilide of formula (1-1)

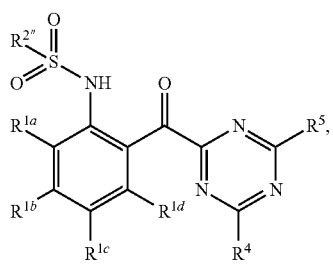

(1-1)

in which
R$^{1a}$ to R$^{1d}$, R$^{2''}$ and also R$^4$ and R$^5$ are as defined for formula (4-1),
and the oxidation products of formula (1-1) are reacted in a fourth step by
alkylation to give an N-alkyl-N-[2-(1,3,5-triazin-2-ylcarbonyl)phenyl]alkanesulfonamide of formula (4-1)

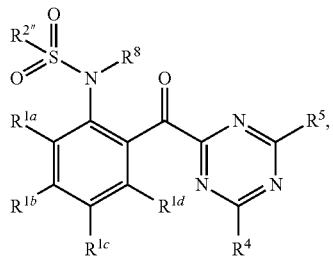

(4-1)

in which
R$^{1a}$ to R$^{1d}$, R$^{2''}$, R$^4$, R$^5$ and R$^8$ are as defined above for formula (4-1),
where the alkylation reagent used is
X—R$^8$, where X is chlorine, bromine or iodine, and R$^8$ is as defined above for formula (4-1), or
(R$^8$)$_2$SO$_4$, in which R$^8$ is as defined above for formula (4-1).

The sulfonylation takes place in the presence of
an imidazole base substituted in the 1 position, or
a base mixture which comprises at least one imidazole base substituted in the 1 position.

Particularly preferred imidazole bases are 1-methyl-1H-imidazole, 1-butyl-1H-imidazole or 1-benzyl-1H-imidazole, which can be used individually or in a mixture, the use of 1-methyl-1H-imidazole being very particularly preferred.

B) Process for the preparation of N-alkyl-N-[2-(1,3,5-triazin-2-ylcarbonyl)phenyl]alkanesulfonamides of formula (4-1) in which the compounds of formula (6-1) used as starting material are prepared in a process step preceding the process for the preparation of compounds of formula (4-1), where, starting from a 3-(alkylsulfanyl)-1,3-dihydro-2H-indol-2-one of formula (7-1),

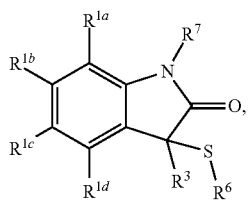

(7-1)

in which
R$^{1a}$ to R$^{1d}$ are as defined for formula (4-1),
R$^3$ is hydrogen,
R$^7$ is hydrogen, and
R$^6$ is an unsubstituted or substituted (C$_1$-C$_{14}$)-alkyl, (C$_3$-C$_7$)-cycloalkyl, benzyl or a CH$_2$—C(O)O—(C$_1$-C$_6$)-alkyl,
is converted by
reduction to give a 1,3-dihydro-2H-indol-2-one (6-1))

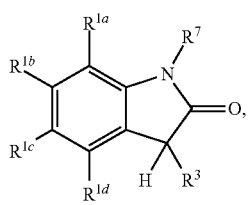

(6-1)

in which
R$^{1a}$ to R$^{1d}$, R$^3$ and R$^7$ are as defined for formula (7-1).

During the reduction,
a) a compound of formula (7-1) is dissolved or suspended in a polar solvent,
b) a sulfur-containing salt is added to the solution or the suspension, and
c) the reaction mixture is heated under reflux at a temperature which corresponds at most to the boiling temperature of the polar solvent.

The particularly preferred sulfur-containing salts are sodium salts selected from the group consisting of sodium bisulfite, sodium sulfite, sodium thionite, sodium dithionite and sodium thiosulfate.

As already mentioned, the herbicidal effect (see WO 2007/031208 A2) and fungicidal effect (see WO 2006/008159 A1) of N-alkyl-N-[2-(1,3,5-triazin-2-ylcarbonyl)

phenyl]alkanesulfonamides of formula (4-1) has been known for a relatively long time.

Consequently, it is demonstrated by scheme 3 and processes A) and B) that triazinyl-substituted oxindoles of formula (3) are suitable as intermediates for producing crop protection agents, in particular herbicides and fungicides.

The invention therefore also provides the use of the compounds of formulae (3) or salts thereof (3") prepared according to the invention for producing active ingredients from agriculture or of intermediates for producing fine chemicals and active ingredients from agriculture, particularly crop protection agents.

Preference is given to the use of compounds of formulae (3) or salts thereof (3") as intermediates for producing N-[2-(1,3,5-triazin-2-ylcarbonyl)phenyl]alkyl-sulfonamides.

The examples below illustrate the invention in more detail without, however, limiting its subject matter to these examples.

In the examples below, quantitative data is by weight, unless otherwise specifically defined (in the description, % by weight=percent by weight was used analogously for this). For measurement units, physical parameters and the like, customary abbreviations are used, for example h=hour(s), m.p.=melting point, l=liter, ml=milliliter, g=gram, min=minute(s), in vacuo="in a vacuum"=under reduced pressure, of theory=percent yield according to the theory.

Example 1

Preparation of 3-(4,6-dimethoxy-1,3,5-triazin-2-yl)-7-fluoro-1,3-dihydro-2H-indol-2-one

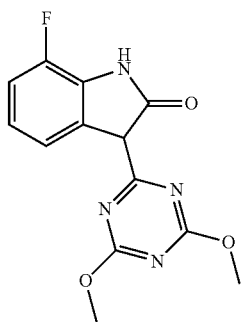 [SMILES: COc1nc(OC)nc(C2C(=O)Nc3c(F)cccc32)n1]

Variant A:

7-Fluoro-1,3-dihydro-2H-indol-2-one (100 g) is introduced as initial charge in 600 ml of N,N-dimethylacetamide and cooled to ca. 0° C. with ice/methanol cooling. A solution of potassium hydroxide (43.2 g) and potassium carbonate (143 g) in 600 ml of water is added and the mixture is briefly after-stirred. Then, 2-chloro-4,6-dimethoxy-1,3,5-triazine (140.8 g) is added and in each case 100 ml of water and N,N-dimethylacetamide are used for after-rinsing. The cooling bath is removed, the mixture heats up to ca. 30° C. It is stirred for 18 hours at room temperature. After adding 150 ml of toluene, dilute hydrochloric acid (ca. 700 ml) is used to adjust the pH to 3-4 and at the same time some antifoam (Fluowet PL 80) is added. The solid is filtered off with suction, washed three times with in each case 250 ml of water and twice with in each case 250 ml of heptane and dried in vacuo at 55° C. This gives the title compound as solid in a purity of 96.6% (187.5 g, 95% of theory).

LC-MS: M+H=291 (100%).

$^1$H NMR (400 MHz, DMSO-D$_6$): δ (ppm)=11.37 (s, 1H), 7.64 (d, 1H), 6.97 (dt, 1H), 6.86 (dd, 1H), 4.05 (s, 6H).

Variant B:

7-Fluoro-1,3-dihydro-2H-indol-2-one (50 g) is introduced as initial charged in 400 ml of acetone and potassium hydroxide (21.5 g) is added. Then, 2-chloro-4,6-dimethoxy-1,3,5-triazine (70.06 g) is added, followed by rinsing with 100 ml of acetone. The reaction mixture is stirred at reflux for one hour, the heating bath is removed and potassium hydroxide (21.5 g) is added in portions. The mixture is then stirred for a further two hours at reflux. The mixture is cooled to 25° C., ten percent strength hydrochloric acid (140 ml) is added, and the mixture is diluted with 250 ml of water and after-stirred for one hour. The solid is filtered off with suction, washed twice with in each case 100 ml of water/acetone (3:1) and dried in vacuo at 50° C. This gives the title compound as solid in a purity of 96.2% (80.09 g, 81% of theory). The NMR signals of the product agree with the signals of the product obtained according to Variant A.

Variant C:

7-Fluoro-1,3-dihydro-2H-indol-2-one (12 g) and 2-chloro-4,6-dimethoxy-1,3,5-triazine (16.5 g) are introduced as initial charge at room temperature in 160 ml of formamide, and potassium carbonate (24.3 g) is added in three equal portions over the course of 1.5 hours. The reaction mixture is after-stirred for 4-5 hours at room temperature. The mixture is added to 500 ml of water and adjusted to pH 3 with dilute hydrochloric acid. The solid is filtered off with suction and washed with water, then with acetonitrile, and dried in vacuo. This gives the title compound as solid in an HPLC purity of 98% area (93.0 g, 80% of theory). The NMR signals of the product agree with the signals of the product obtained according to Variant A.

Variant D:

7-Fluoro-1,3-dihydro-2H-indol-2-one (60 g) and 2-chloro-4,6-dimethoxy-1,3,5-triazine (94.6 g) are introduced as initial charge in 315 ml of THF and cooled to 5° C. With ice cooling, a solution of potassium hydroxide (58.1 g) in 105 ml of water is added over the course of 2 hours at an internal temperature of 0-15° C., and the mixture is after-stirred for 4 hours. The solid is filtered off with suction, washed with water (2×150 ml) and dried in vacuo. This gives the title compound as solid in a purity of 98.2% (21.1 g, 91% of theory). The NMR signals of the product agree with the signals of the product obtained according to Variant A.

Variant E:

7-Fluoro-1,3-dihydro-2H-indol-2-one (30 g) and 2-chloro-4,6-dimethoxy-1,3,5-triazine (43.9 g) are introduced as initial charge at 60° C. in acetonitrile, and sodium hydroxide (16.8 g) is added in four equal portions over the course of 40 min. The mixture was after-stirred for a further 90 min at this temperature and then cooled to 40° C. Hydrochloric acid (20% strength, 42 g) and water (160 g) are added. After a further 30 min, the resulting suspension was filtered and the filter residue was washed with acetonitrile. Drying in vacuo (50° C., <200 mbar) gave the title compound as solid with an HPLC purity of 96.9% (48.0 g; 85% of theory). The NMR signals of the product agree with the signals of the product obtained according to Variant A.

Variant F:

7-Fluoro-1,3-dihydro-2H-indol-2-one (10 g; 1 eq.) is introduced as initial charge in 100 ml of THF and 100 ml of N,N-dimethylformamide at room temperature under nitrogen, and sodium hydride (2.63 g; 60% in mineral oil, 1 eq.) is added. The mixture is after-stirred for 30 min and 2-chloro-4,6-dimethoxy-1,3,5-triazine (4.72 g; 0.4 eq.) is added in one portion. The mixture is after-stirred for 10 min at 35° C. and for 2 hours at 80° C. The mixture is cooled and concentrated by evaporation in vacuo (50° C. bath temperature, 10 mbar). 200 ml of water are added to the residue, and the pH is adjusted to 3-4 with hydrochloric acid. The precipitated solid is filtered off with suction; the filtrate comprises virtually no product according to HPLC. The filter residue is washed with water (50 ml), stirred in water-moist form with 75 ml of acetonitrile, filtered off with suction, after-washed with acetonitrile and dried in vacuo. This gives the title compound as solid in an HPLC purity of 97% area (7.62 g; 39% of theory, based on the 7-fluoro-1, 3-dihydro-2H-indol-2-one used or 97% of theory, based on the 2-chloro-4,6-dimethoxy-1,3,5-triazine used). The NMR signals of the product agree with the signals of the product obtained according to Variant A.

Variant G:

7-Fluoro-1,3-dihydro-2H-indol-2-one (10 g; 1 eq.) and 2-chloro-4,6-dimethoxy-1,3,5-triazine (14.1 g; 1.2 eq.) are reacted analogously to Example 1 Variant F. This gives the title compound as solid in an HPLC purity of 97% area (7.65 g; 39% of theory, based on the 7-fluoro-1,3-dihydro-2H-indol-2-one used). The NMR signals of the product agree with the signals of the product obtained according to Variant A.

Variant H (Procedure Analogous to Organic Letters (2010) 2306 Examples in Table 4 (Supplement Page S-12 General Procedure):

7-Fluoro-1,3-dihydro-2H-indol-2-one (2.5 g; 1 eq.), 2-chloro-4,6-dimethoxy-1,3,5-triazine (3.5 g; 1.2 eq.) and caesium carbonate (5.6 g, 1 eq.) are introduced as initial charge under nitrogen, and 95 ml of N,N-dimethylformamide (water content <0.1%) are added. The mixture is heated to 65° C. and stirred under nitrogen for 5 hours at 65° C. HPLC analysis (detection at 210 nm, data in area percent, solvent signal is not integrated) reveals 16% 7-fluoro-1,3-dihydro-2H-indol-2-one, 19% of the title compound (3-(4, 6-dimethoxy-1,3,5-triazin-2-yl)-7-fluoro-1,3-dihydro-2H-indol-2-one), 57% of a main secondary component (or of a mixture of two or more main secondary components) and further small secondary components. The mixture is cooled to room temperature and added to 200 ml of saturated ammonium chloride solution. Ethyl acetate is added until two clear phases are formed (in total 2900 ml), the phases are separated, and the organic phase is washed with water (2×150 ml) and 150 ml of sodium chloride solution and dried over magnesium sulfate. The solvent is removed in vacuo, during which a solid precipitates out. The solid is filtered off and washed with some ethyl acetate. This gives 1.92 g of a mixture which, according to HPLC analysis (detection at 210 nm, data in area percent), consists to 56% (22% of theory) of the title compound and to 43% of a secondary component. An LC-MS of the mixture reveals the presence of the title compound (M+H=291) and of a secondary component with a mass of 429 (M+H=430), which is probably a diarylated product. The identity of the title compound present in the product mixture can be confirmed by spiking the reaction mixture with authentic material, prepared as in Example 1 variant A, and comparing the UV absorptions, and also by NMR spectroscopy of the mixture.

The filtrate is concentrated by evaporation in vacuo, giving 3.6 g of residue, which still contains DMF. HPLC analysis (detection at 210 nm, data in area percent, solvent signal is not integrated) of the residue reveals 19% 7-fluoro-1,3-dihydro-2H-indol-2-one, 1% of the title compound, 68% of a mixture of two main secondary components and further small secondary components. An LC-MS of the residue reveals the presence of the title compound (M+H=291.4%) and two secondary components with a mass of 429 (M+H=430, 19% and 49%), which are presumably diarylated products.

Example 2

Preparation of 3-(4,6-dimethoxy-1,3,5-triazin-2-yl)-1,3-dihydro-2H-indol-2-one

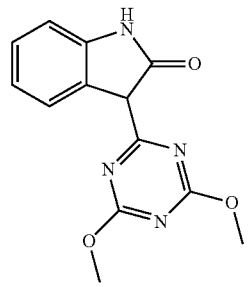 [SMILES: COc1nc(OC)nc(C2C(=O)Nc3ccccc32)n1]

Variant A:

1,3-Dihydro-2H-indol-2-one (3.0 g) and 2-chloro-4,6-dimethoxy-1,3,5-triazine (7.52 g) are reacted analogously to Example 1 Variant C. This gives the title compound as solid in an HPLC purity of 91% area (4.79 g, 73% of theory).

LC-MS: M+H=273 (91.8%).

$^1$H NMR (400 MHz, DMSO-D$_6$): δ (ppm)=10.96 (s, 1H), 7.78-7.84 (m, 1H), 6.95-7.04 (m, 3H), 4.04 (s, 6H).

Variant B:

1,3-Dihydro-2H-indol-2-one (0.80 g; 1 eq.) is introduced as initial charge in 8 ml of THF and 8 ml of N,N-dimethylformamide at room temperature under nitrogen, and sodium hydride (0.24 g; 60% in mineral oil, 1 eq.) is added. The mixture is after-stirred for 30 min, and 2-chloro-4,6-dimethoxy-1,3,5-triazine (0.42 g; 0.4 eq.) is added in one portion. The mixture is after-stirred for 2 hours at room temperature. The mixture is cooled and concentrated by evaporation in vacuo (40° C. bath temperature). 25 ml of water are added to the residue and hydrochloric acid is used to adjust the pH to 3-4. The precipitated solid is filtered off with suction, the filtrate comprises virtually no product according to HPLC. The filter residue is washed with water, stirred in the water-moist state with 10 ml of acetonitrile and filtered off with suction. This gives the title compound as solid in an HPLC purity of 90% area (0.61 g; 34% of theory, based on the 1,3-dihydro-2H-indol-2-one used, or 84% of theory, based on the 2-chloro-4,6-dimethoxy-1,3,5-triazine used). The NMR signals of the product agree with the signals of the product obtained according to Variant A.

Variant C:

1,3-Dihydro-2H-indol-2-one (0.80 g; 1 eq.) and 2-chloro-4,6-dimethoxy-1,3,5-triazine (1.27 g; 1.2 eq.) are reacted analogously to Example 1 Variant F. This gives the title compound as solid in an HPLC purity of 78% area (0.59 g; 30% of theory, based on the 1,3-dihydro-2H-indol-2-one used). The NMR signals of the product agree with the signals of the product obtained according to Variant A.

Example 3

Preparation of 3-(4,6-dimethoxy-1,3,5-triazin-2-yl)-5,7-difluoro-1,3-dihydro-2H-indol-2-one

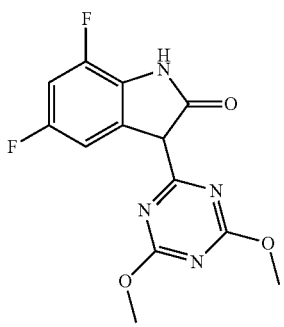 [SMILES: COc1nc(OC)nc(C2C(=O)Nc3c(F)cc(F)cc32)n1]

5,7-Difluoro-1,3-dihydro-2H-indol-2-one (1.69 g) and 2-chloro-4,6-dimethoxy-1,3,5-triazine (2.13 g) are reacted analogously to Example 1 Variant A. This gives the title compound as solid in an HPLC purity of 93% area (2.82 g, 85% of theory).

LC-MS: M+H=309 (97%).

$^1$H NMR (400 MHz, DMSO-D$_6$): δ (ppm)=11.42 (s, 1H), 7.35 (dd, 1H), 6.86 (dt, 1H), 4.04 (s, 6H).

Example 4

Preparation of 3-(4,6-dimethoxy-1,3,5-triazin-2-yl)-7-chloro-1,3-dihydro-2H-indol-2-one

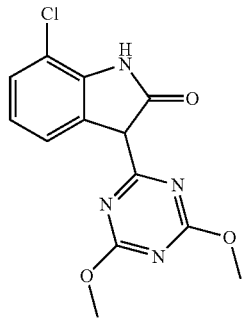

7-Chloro-1,3-dihydro-2H-indol-2-one (101.5 g) and 2-chloro-4,6-dimethoxy-1,3,5-triazine (152 g) are reacted analogously to Example 1 Variant A. This gives the title compound as solid in an HPLC purity of 99% area (181.9 g, 97% of theory).

LC-MS: M+H=307 (96.7%).

$^1$H NMR (400 MHz, DMSO-D$_6$): δ (ppm)=11.39 (s, 1H), 7.77 (d, 1H), 6.98-7.06 (m, 2H), 4.05 (s, 6H).

Example 5

Preparation of 3-(4,6-dimethoxy-1,3,5-triazin-2-yl)-5-fluoro-1,3-dihydro-2H-indol-2-one

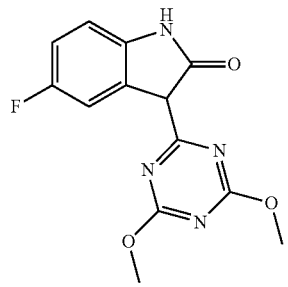 [SMILES: COc1nc(OC)nc(C2C(=O)Nc3ccc(F)cc32)n1]

5-Fluoro-1,3-dihydro-2H-indol-2-one (10 g) and 2-chloro-4,6-dimethoxy-1,3,5-triazine (15.5 g) are reacted analogously to Example 1 Variant A. This gives the title compound as solid in an HPLC purity of 92% area (19 g, 91% of theory).

LC-MS: M+H=291 (90%).

$^1$H NMR (400 MHz, DMSO-D$_6$): δ (ppm)=11.06 (s, 1H), 7.53 (dd, 1H), 6.95 (dd, 1H), 6.82 (dt, 1H), 4.06 (s, 6H).

Example 6

Preparation of 3-(4,6-dimethoxy-1,3,5-triazin-2-yl)-7-methoxy-1,3-dihydro-2H-indol-2-one

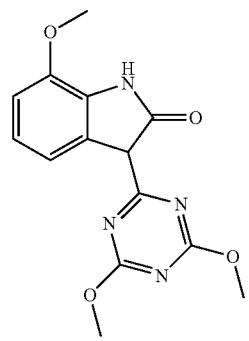 [SMILES: COc1nc(OC)nc(C2C(=O)Nc3c(OC)cccc32)n1]

7-Methoxy-1,3-dihydro-2H-indol-2-one (1.24 g) and 2-chloro-4,6-dimethoxy-1,3,5-triazine (1.84 g) are reacted analogously to Example 1 Variant A. This gives the title compound as solid in an HPLC purity of 87% area (1.04 g, 43% of theory).

LC-MS: M−H=301 (84%).

$^1$H NMR (400 MHz, DMSO-D$_6$): δ (ppm)=11.36 (s, 1H), 7.52 (d, 1H), 6.96 (t, 1H), 6.71 (d, 1H), 4.04 (s, 6H), 3.85 (s, 3H).

Example 7

Preparation of 3-(4,6-dimethoxy-1,3,5-triazin-2-yl)-5-methoxy-1,3-dihydro-2H-indol-2-one

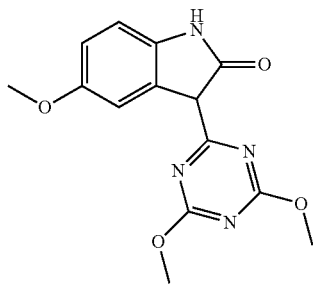

5-Methoxy-1,3-dihydro-2H-indol-2-one (1.59 g) and 2-chloro-4,6-dimethoxy-1,3,5-triazine (1.97 g) are reacted analogously to Example 1 Variant A. This gives the title compound as solid in an HPLC purity of 92% area (1.39 g, 53% of theory).

LC-MS: M+H=303 (94%).

$^1$H NMR (400 MHz, DMSO-D$_6$): δ (ppm)=10.89 (s, 1H), 7.43 (d, 1H), 6.89 (d, 1H), 6.61 (dd, 1H), 4.06 (s, 6H), 3.74 (s, 3H).

Example 8

Preparation of 7-fluoro-3-(4-methoxy-6-methyl-1,3,5-triazin-2-yl)-1,3-dihydro-2H-indol-2-one

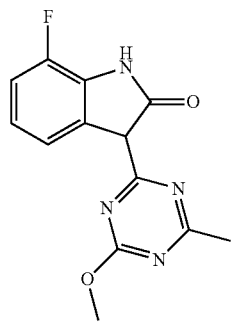 [SMILES: COc1nc(C)nc(C2C(=O)Nc3c(F)cccc32)n1]

7-Fluoro-1,3-dihydro-2H-indol-2-one (3.05 g) and 2-chloro-4-methoxy-6-methyl-1,3,5-triazine (6.59 g) are reacted analogously to Example 1 Variant A. This gives the title compound as solid in an HPLC purity of 85% area (4.73 g, 73% of theory).

LC-MS: M+H=275 (72%).

$^1$H NMR (400 MHz, DMSO-D$_6$): δ (ppm)=11.02 (s, 1H), 7.59 (d, 1H), 6.91-6.98 (m, 1H), 6.85 (t, 1H), 4.06 (s, 3H), 2.46 (s, 3H).

Example 9

Preparation of 3-(4,6-diethoxy-1,3,5-triazin-2-yl)-7-fluoro-1,3-dihydro-2H-indol-2-one

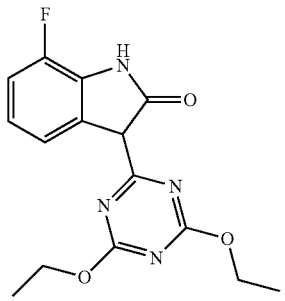 [SMILES: CCOc1nc(OCC)nc(C2C(=O)Nc3c(F)cccc32)n1]

7-Fluoro-1,3-dihydro-2H-indol-2-one (1.0 g) is introduced as initial charge in 10 ml of N,N-dimethylacetamide. A solution of potassium carbonate (1.8 g) and potassium hydroxide (0.3 g) in 10 ml of water is added and the mixture is briefly after-stirred. Then, a solution of 2-chloro-4,6-diethoxy-1,3,5-triazine (3.0 g, ca. 50% purity) in 10 ml of N,N-dimethylacetamide, and 10 ml of water are added. A solid separates out from the clear yellow solution. The mixture is stirred at room temperature and further 2-chloro-4,6-diethoxy-1,3,5-triazine (1 g, ca. 50% purity) is added in two portions after 2 and 18 hours. The mixture is stirred for a further 3 hours at 30° C., admixed with 10 ml of toluene, adjusted to pH 1-2 with hydrochloric acid (10%) and after-stirred for 30 min. The solid is filtered off with suction, washed twice alternately with water and heptane and dried. This gives the title compound as solid in an HPLC purity of 99% area (1.53 g, 72% of theory).

LC-MS: M+H=319 (86%).

$^1$H NMR (400 MHz, DMSO-D$_6$): δ (ppm)=11.3 (s, 1H), 7.59 (d, 1H), 6.96 (dd, 1H), 6.93-7.00 (m, 1H), 4.50 (q, 4H), 1.37 (t, 6H).

Example 10

Preparation of 2-[(4,6-dimethoxy-1,3,5-triazin-2-yl)oxy]-3-phenyl-1H-indol (Procedure Analogous to Organic Letters (2010) 2306 Examples in Table 4 (Supplement Page S-12 General Procedure)

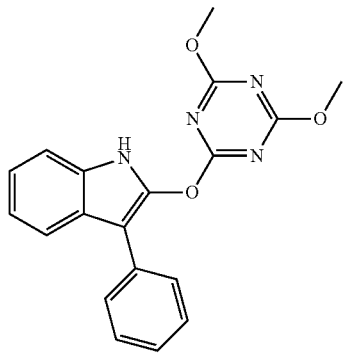 [SMILES: COc1nc(OC)nc(Oc2[nH]c3ccccc3c2-c2ccccc2)n1]

3-phenyl-1,3-dihydro-2H-indol-2-one (0.25 g; 1 eq.), 2-chloro-4,6-dimethoxy-1,3,5-triazine (0.20 g; 1 eq.) and caesium carbonate (0.37 g, 1 eq.) are introduced as initial charge, and 20 ml of N,N-dimethylformamide (water content <0.1%) are added. The mixture is stirred for 90 min at 23° C. HPLC analysis (detection at 210 nm, data in area percent, solvent signal is not integrated) reveals 3% 3-phenyl-1,3-dihydro-2H-indol-2-one, 1.5% 2-chloro-4,6-dimethoxy-1,3,5-triazine, 68% of a main product and small secondary components. The mixture is added to 100 ml of water and adjusted to pH 4 with dilute hydrochloric acid. The precipitated solid is filtered off and washed with water. This gives a mixture which, according to HPLC analysis (detection at 210 nm, data in area percent), consists to 71% of a main product (0.37 g, 66% of theory). 100 mg of the mixture are purified by column chromatography (eluant ethyl acetate and n-heptane 1:1) and the combined product fractions are concentrated by evaporation in vacuo. This gives the reaction product as a colorless solid in an HPLC purity of 93% area. Structural elucidation by 2D-NMR shows that it is not the product arylated in the 3 position (3-(4,6-dimethoxy-1,3,5-triazin-2-yl)-3-phenyl-1,3-di-hydro-2H-indol-2-one), but the O-arylated product (2-[(4,6-dimethoxy-1,3,5-triazin-2-yl)oxy]-3-phenyl-1H-indol).

LC-MS: M+H=349 (96%).

1H-NMR (600 MHz, CDCl$_3$): δ (ppm)=8.95 (s, broad, 1H), 7.82 (d, 1H), 7.65 (dd, 2H), 7.41 (t, 2H), 7.37 (d, 1H), 7.24 (q, 2H), 7.19 (t, 1H), 3.98 (s, 6H).

The invention claimed is:

1. A method of producing an N-sulfonyl-substituted 3-triazinyloxindole, the method comprising sulfonylation of a compound of formula (3)

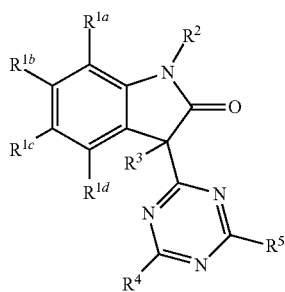

(3)

or a salt thereof (3")

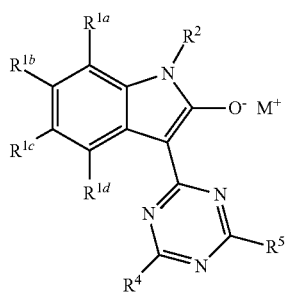

(3")

in which
$R^{1a}$ to $R^{1d}$, independently of one another, are selected from the group consisting of hydrogen, fluorine, chlorine, bromine, iodine, and also from ($C_1$-$C_6$)-alkyl, where the alkyl radical is unsubstituted or is substituted by at least one substituent selected from the group consisting of fluorine, chlorine, ($C_1$-$C_4$)-alkoxy or ($C_3$-$C_7$)-cycloalkyl, ($C_3$-$C_7$)-cycloalkyl, where the cycloalkyl radical is unsubstituted or is substituted by at least one substituent selected from the group consisting of fluorine, chlorine, ($C_1$-$C_4$)-alkyl or ($C_3$-$C_7$)-cycloalkyl or ($C_1$-$C_4$)-alkoxy, ($C_1$-$C_6$)-alkoxy, where the alkoxy radical is unsubstituted or is substituted by at least one substituent selected from the group consisting of fluorine, chlorine, ($C_1$-$C_4$)-alkoxy or ($C_3$-$C_7$)-cycloalkyl, ($C_3$-$C_7$)-cycloalkoxy, where the cycloalkoxy radical is unsubstituted or is substituted by at least one substituent selected from the group consisting of fluorine, chlorine, ($C_1$-$C_4$)-alkyl or ($C_1$-$C_4$)-alkoxy, ($C_1$-$C_6$)-alkylthio, where the alkylthio radical is unsubstituted or is substituted by at least one substituent selected from the group consisting of fluorine, chlorine, ($C_1$-$C_4$)-alkyl or ($C_1$-$C_4$)-alkoxy, ($C_3$-$C_7$)-cycloalkylthio, where the cycloalkylthio radical is unsubstituted or is substituted by at least one substituent selected from the group consisting of fluorine, chlorine, ($C_1$-$C_4$)-alkyl or ($C_1$-$C_4$)-alkoxy, and also from phenyl or 1-naphthyl or 2-naphthyl or a five- or six-membered heteroaromatic ring comprising from 1 to 2 heteroatoms, where said heteroatoms, independently of one another, are selected from the group consisting of O or N and where the aryl or heteroaryl radical is unsubstituted or is substituted by at least one substituents selected from the group consisting of fluorine, chlorine, bromine, iodine, ($C_1$-$C_4$)-alkyl, ($C_1$-$C_4$)-alkoxy or ($C_3$-$C_7$)-cycloalkyl or ($C_1$-$C_4$)-alkylthio, and $R^2$ is
hydrogen,
$R^3$ is
hydrogen,
$R^4$ and $R^5$, independently of one another, are in each case
hydrogen,
($C_1$-$C_6$)-alkyl, where the alkyl radical is unsubstituted or is substituted by at least one substituent selected from the group consisting of fluorine, chlorine, ($C_1$-$C_4$)-alkoxy or ($C_3$-$C_7$)-cycloalkyl,
($C_1$-$C_6$)-alkoxy, where the alkoxy radical is unsubstituted or is substituted by at least one substituent selected from the group consisting of fluorine, chlorine, ($C_1$-$C_4$)-alkoxy or ($C_3$-$C_7$)-cycloalkyl,
where, in said salt of formula (3"),
M is Li, Na, K, N($R^c$)$_4$, where $R^c$=H or $C_1$-$C_6$ alkyl, Cs, Ba, Mg, Ca and Zn, and number of counter ions $M^+$ is governed by a particular charge such that an overall neutral compound of formula (3") is formed.

* * * * *